(12) United States Patent
Kim et al.

(10) Patent No.: US 11,076,826 B2
(45) Date of Patent: Aug. 3, 2021

(54) ULTRASOUND IMAGING APPARATUS AND CONTROL METHOD THEREOF

(71) Applicant: SAMSUNG MEDISON CO., LTD., Gangwon-Do (KR)

(72) Inventors: Nam-Woong Kim, Seoul (KR); Yong-cheol Hyeon, Seoul (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 1144 days.

(21) Appl. No.: 15/482,026

(22) Filed: Apr. 7, 2017

(65) Prior Publication Data
US 2018/0103925 A1    Apr. 19, 2018

(30) Foreign Application Priority Data

Oct. 14, 2016  (KR) .................. 10-2016-0133764

(51) Int. Cl.
| | |
|---|---|
| *A61B 8/00* | (2006.01) |
| *A61B 8/08* | (2006.01) |
| *A61B 8/14* | (2006.01) |
| *H01F 17/00* | (2006.01) |
| *H01L 49/02* | (2006.01) |

(52) U.S. Cl.
CPC .................. *A61B 8/14* (2013.01); *A61B 8/00* (2013.01); *A61B 8/4405* (2013.01); *A61B 8/4483* (2013.01); *A61B 8/54* (2013.01); *A61B 8/467* (2013.01); *A61B 8/5207* (2013.01); *H01F 17/0013* (2013.01); *H01L 28/10* (2013.01)

(58) Field of Classification Search
CPC .............................. H01L 28/10; H01F 17/0013
See application file for complete search history.

(56) References Cited

U.S. PATENT DOCUMENTS

| | | | |
|---|---|---|---|
| 7,458,935 B2 | 12/2008 | Cerofolini | |
| 2003/0105399 A1 | 6/2003 | Morsy et al. | |
| 2004/0140528 A1* | 7/2004 | Kim | .................... H01L 23/5227 |
| | | | 257/537 |

FOREIGN PATENT DOCUMENTS

| | | |
|---|---|---|
| JP | 63221241 A  *  9/1988 | |
| KR | 10-2009-0025618 A | 3/2009 |
| KR | 10-2010-0118157 A | 11/2010 |

(Continued)

OTHER PUBLICATIONS

Extended European Search Report dated Jul. 21, 2017 issued in European Patent Application No. 17153686.5.

*Primary Examiner* — Boniface N Nganga
(74) *Attorney, Agent, or Firm* — Morgan, Lewis & Bockius LLP

(57) ABSTRACT

It is an aspect of the present disclosure to provide an ultrasound imaging apparatus of transmitting/receiving an ultrasound signal to/from an ultrasound probe, and successively changing inductance using a plurality of inductors for impedance matching between the ultrasound probe and a main body during a transmission/reception time period of the ultrasound signal, and a control method of the ultrasound imaging apparatus.

The ultrasound imaging apparatus may include an ultrasound probe; a signal transceiver configured to transmit/receive an ultrasound signal to/from the ultrasound probe; and a variable inductor device configured to successively change inductance for impedance matching with the ultrasound probe during a transmission/reception time period of the ultrasound signal.

8 Claims, 12 Drawing Sheets

(56) References Cited

FOREIGN PATENT DOCUMENTS

| | | |
|---|---|---|
| KR | 10-2011-0092558 A | 8/2011 |
| KR | 10-1341092 B1 | 12/2013 |
| KR | 10-2016-0109886 A | 9/2016 |
| WO | 2013/100246 A1 | 7/2013 |

\* cited by examiner

ULTRASOUND IMAGING APPARATUS AND CONTROL METHOD THEREOF

CROSS-REFERENCE TO RELATED APPLICATION

This application claims the benefit of Korean Patent Application No. 10-2016-0133764, filed on Oct. 14, 2016 in the Korean Intellectual Property Office, the disclosure of which is incorporated herein by reference.

BACKGROUND

1. Field

Embodiments of the present disclosure relate to an ultrasound imaging apparatus, and a control method thereof.

2. Description of the Related Art

An ultrasound imaging apparatus is equipment of irradiating ultrasonic waves toward a target part inside an object from the surface of the object, and receiving echo ultrasonic waves reflected from the target part so as to non-invasively acquire slice images about soft tissue of the object or images about blood vessels of the object.

The ultrasound imaging apparatus has advantages that it is a compact, low-priced apparatus compared to other medical imaging apparatuses, such an X-ray imaging apparatus, a Computerized Tomography (CT) scanner, a Magnetic Resonance Image (MRI) apparatus, and a nuclear medicine diagnosis apparatus, and it can display diagnosis images in real time. Also, the ultrasound imaging apparatus has high safety since there is no risk for patients to be exposed to radiation. For the advantages, the ultrasound imaging apparatus is widely used for diagnosis of the heart, abdomen, and urinary organs, as well as diagnosis of obstetrics & gynecology clinic.

The ultrasound imaging apparatus includes a probe to transit ultrasonic waves to an object and to receive echo ultrasonic waves reflected from the object, in order to acquire an ultrasound image of the object.

Also, ultrasonic waves transmitted to an object (medium) attenuate when moving through the object so that the sound pressure of the ultrasonic waves is lowered, and particularly, attenuation of a high frequency component increases sharply in proportion to the movement distance of the ultrasonic waves, which greatly lowers the center frequency of received echo ultrasonic waves.

SUMMARY

Therefore, it is an aspect of the present disclosure to provide an ultrasound imaging apparatus of transmitting/receiving an ultrasound signal to/from an ultrasound probe, and successively changing inductance using a plurality of inductors for impedance matching between the ultrasound probe and a main body during a transmission/reception time period of the ultrasound signal, and a control method of the ultrasound imaging apparatus.

Additional aspects of the disclosure will be set forth in part in the description which follows and, in part, will be obvious from the description, or may be learned by practice of the disclosure.

In accordance with one aspect of the present disclosure, An ultrasound imaging apparatus may include an ultrasound probe; a signal transceiver configured to transmit/receive an ultrasound signal to/from the ultrasound probe; and a variable inductor device configured to successively change inductance for impedance matching with the ultrasound probe during a transmission/reception time period of the ultrasound signal.

The variable inductor device may successively changes inductance according to a change in center frequency of the ultrasound signal received from the ultrasound probe.

The variable inductor device may comprise a plurality of inductors.

The variable inductor device may comprise at least one switch connecting the plurality of inductors to one another, and selectively connects at least one of the plurality of inductors according to operation of the at least one switch to change the inductance.

The plurality of inductors may be stacked.

The plurality of inductors may have difference inductance values.

The at least one switch may be disposed between the plurality of inductors.

The at least one switch may include at least one of a MEMS switch and a FET switch.

A variable range of the inductance may be decided within a range from 0 µH to 11 µH.

The plurality of inductors may include 8 inductors having inductance values of 0.1 µH, 0.2 µH, 0.3 µH, 0.4 µH, 1 µH, 2 µH, 3 µH, and 4 µH, respectively, or 7 inductors having inductance values of 0.1 µH, 0.2 µH, 0.3 µH, 0.4 µH, 2 µH, 3 µH, and 4 µH, respectively.

The ultrasound imaging apparatus may further include a probe switch box to which the ultrasound probe is connected, wherein the variable inductor device is installed in the probe switch box.

In accordance with another aspect of the present disclosure, A method of controlling an ultrasound imaging apparatus may include transmitting/receiving an ultrasound signal to/from an ultrasound probe; and successively changing inductance for impedance matching with the ultrasound probe during a transmission/reception time period of the ultrasound signal.

The changing of the inductance may include successively changing inductance according to a change in center frequency of the ultrasound signal received from the ultrasound probe.

The changing of the inductance may include using a plurality of inductors.

The changing of the inductance may include using at least one switch connecting the plurality of inductors to one another; and selectively connecting at least one of the plurality of inductors according to operation of the at least one switch to change the inductance.

The plurality of inductors may be stacked.

The plurality of inductors may have different inductance values.

The at least one switch may be disposed between the plurality of inductors.

The at least one switch may include at least one of a MEMS switch and a FET switch.

A variable range of the inductance may be decided within a range from 0 µH to 11 µH.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
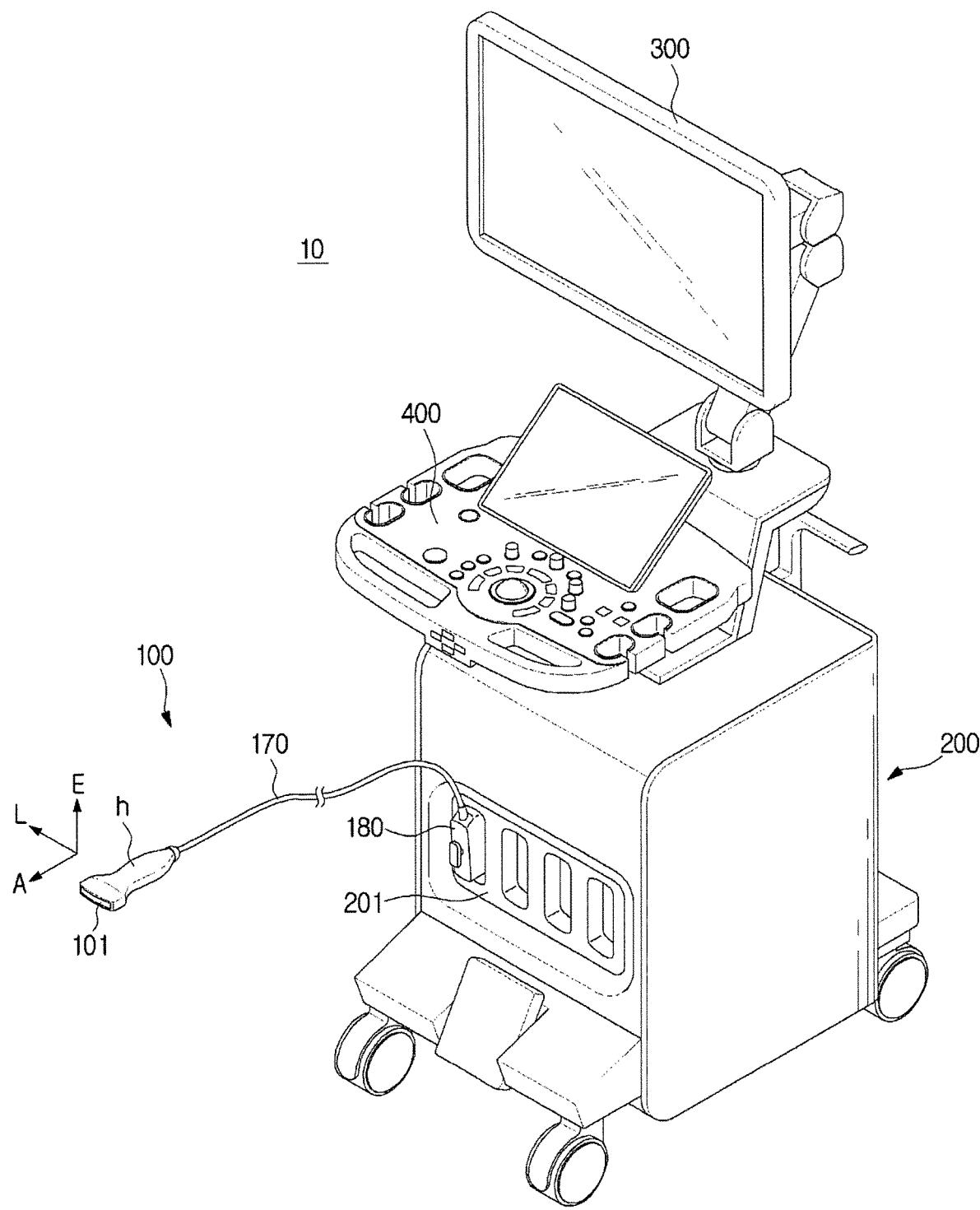
FIG. 1 is a perspective view of an ultrasound imaging apparatus according to an embodiment of the present disclosure.

Purposes, specific advantages, and novel features of the present disclosure will become apparent from the following detailed description and the accompanying drawings, which are associated with exemplary embodiments. In this specification, the same reference numerals are used throughout the different drawings to designate the same components. Further, when it is determined that the detailed description of the known art related to the present disclosure may obscure the gist of the present invention, the detailed description will be omitted. Also, it will be understood that, although the terms first, second, etc. may be used herein to describe various elements, these elements should not be limited by these terms. These terms are only used to distinguish one element from another. Hereinafter, embodiments of the present disclosure will be described in detail with reference to the appended drawings such that one of ordinary skill in the art can easily understand and embody the present disclosure. However, the present disclosure is not limited to the following embodiments, and may be embodied in a different manner.

Hereinafter, an ultrasound imaging apparatus and a control method thereof will be described in detail with reference to FIGS. 1 to 12.

FIG. 1 is a perspective view of an ultrasound imaging apparatus according to an embodiment of the present disclosure.

Referring to FIG. 1, an ultrasound imaging apparatus 10 may include an ultrasound probe 100 configured to transmit an ultrasound signal to an object ob (see FIG. 4), and to receive an echo ultrasound signal from the object ob to convert the echo ultrasound signal into an electrical signal, and a main body 200 configured to create an ultrasound image based on an ultrasound signal. The main body 200 may connect to the ultrasound probe 100 through a wired/wireless communication network. The main body 200 may be a workstation including a display 300 and an input device 400. Also, the main body 200 may transmit/receive various information to/from an external device through the wired/wireless communication network.

Meanwhile, the ultrasound imaging apparatus 10 may be implemented as equipment used for ultrasonic diagnosis in hospitals, as shown in FIG. 1. However, the ultrasound imaging apparatus 10 is not limited to the equipment as shown in FIG. 1.

For example, the ultrasound imaging apparatus 10 may be implemented as a laptop computer, a desktop computer, a tablet PC, or a smart phone. Also, the ultrasound imaging apparatus 10 may be implemented as a mobile terminal such as Personal Digital Assistant (PDA), or as a wearable terminal in the shape of a watch or glasses, which can be attached/detached on/from a user's body.

However, the ultrasound imaging apparatus 10 is not limited to these, and the ultrasound imaging apparatus 10 can be included in any apparatus that includes a communication unit capable of transmitting/receiving radio signals to/from an external device through a wireless communication network, and can display ultrasound images through a display.

Meanwhile, the object ob may be a human's or animal's living body, or tissue in a living body, such as blood vessels, bonds, and muscles, although not limited to these. That is, the object ob may be anything whose inside structure can be imaged by the ultrasound imaging apparatus 10.

The ultrasound probe 100 may include a transducer module 101 included in a housing h and configured to irradiate ultrasonic waves to the object ob and to receive echo ultrasonic waves reflected from the object ob to convert the ultrasonic waves into electrical pulse signals and vice versa, a male connector 180 physically coupled with a female connector of the main body 200 and configured to transmit/receive signals to/from the main body 200, a cable 170 connecting the transducer module 101 to the male connector 180, and a probe switch box 102 (see FIG. 4) connecting the cable 170 to the main body 200.

Also, the ultrasound probe 100 may connect to at least one of the main body 200 and an external device through a wireless communication network to receive various signals required for controlling the ultrasound probe 100 from the main body 200 or the external device, or to transfer an analog signal or a digital signal corresponding to a received echo ultrasound signal to the main body 200 or the external device.

The wireless communication network means a communication network supporting a wireless communication method for enabling wireless transmission and reception of signals. For example, the wireless communication method may include a communication method, such as 3 Generation (3G) or 4 Generation (4G), to transmit and receive radio signals via a base station, and a communication method, such as Wireless Local Area Network (WLAN), Wireless-Fidelity (WiFi), Bluetooth, Zigbee, Wi-Fi Direct (WFD), Ultra Wideband (UWB), Infrared Data Association (IrDA), Bluetooth Low Energy (BLE), and Near Field Communication (NFC), to enable devices located within a predetermined distance range to directly transmit/receive signals to/from each other. However, the wireless communication method is not limited to the above-mentioned examples, and may include all kinds of communication networks that support transmission and reception of radio signals between the ultrasound probe 100 and the main body 200.

Echo ultrasonic waves may be ultrasonic waves reflected from the objet ob to which ultrasonic waves have been irradiated, and have various frequency bands or energy intensities for creating various ultrasound images according to diagnosis modes.

The transducer module 101 may generate ultrasonic waves according to alternating-current power applied thereto. More specifically, the transducer module 101 may receive alternating-current power from an external power supply or from an internal power storage unit, for example, a battery. A vibrator of the transducer module 101 may vibrate according to the alternating-current power to generate ultrasonic waves.

Three directions forming right angles with respect to the center of the transducer module 101 can be defined as an axis direction A, a lateral direction L, and an elevation direction E, respectively. More specifically, a direction in which ultrasonic waves are irradiated is defined as an axis direction A, a direction in which the transducer module 101 is aligned in a row is defined as a lateral direction L, and the remaining direction perpendicular to the axis direction A and the lateral direction L is defined as an elevation direction E.

One end of the cable 170 may be connected to the transducer module 101, and the other end of the cable 170 may be connected to the male connector 180, so as to connect the transducer module 101 to the male connector 180.

The male connector 180 may be connected to the other end of the cable 170 to be physically coupled with the female connector 201 of the main body 200.

The male connector 180 may transfer electrical signals generated by the transducer module 101 to the female connector 201, or may receive control signals generated by the main body 200 from the female connector 201.

However, if the ultrasound probe 100 is a wireless ultrasound probe, the cable 170 and the male connector 180 may be not needed, and the ultrasound probe 100 may transmit/receive signals to/from the main body 200 through a wireless communication module (not shown) included in the ultrasound probe 100. That is, the ultrasound probe 100 is not limited to the structure shown in FIG. 1.

The main body 200 may perform wireless communication with the ultrasound probe 100 through at least one of a short-range communication module and a mobile communication module.

The short-range communication module means a module for short-range communication within a predetermined distance range. Short-range communication methods include, for example, WLAN, Wi-Fi, Bluetooth, Zigbee, WFD, UWB, IrDA, BLE, NFC, etc., although not limited to these.

The mobile communication module may transmit/receive radio signals to/from at least one of a base station, an external terminal, and a server through a mobile communication network. The radio signals mean signals including various forms of data. That is, the main body 200 may transmit/receive various forms of data to/from the ultrasound probe 100, via at least one of a base station and a server.

For example, the main body 200 may transmit/receive signals including various forms of data to/from the ultrasound probe 100, via a base station, through a mobile communication network such as 3G or 4G. Also, the main body 200 may transmit/receive data to/from a hospital server or other medical apparatuses in a hospital, connected through Picture Archiving and Communication System (PACS). Also, the main body 200 may transmit/receive data according to a Digital Imaging and Communications in Medicine (DICOM) standard, although not limited to this.

Also, the main body 200 may transmit/receive data to/from the ultrasound probe 100 through a wired communication network. The wired communication network means a communication network to enable wired transmission and reception of signals. According to an embodiment, the main body 200 may transmit/receive various signals to/from the ultrasound probe 100 using a wired communication network, such as a Peripheral Component Interconnect (PCI), PCI-express, Universe Serial Bus (USB), etc., although not limited to this.

Hereinafter, a configuration of the ultrasound probe 100 will be described in more detail.

Figure 2:
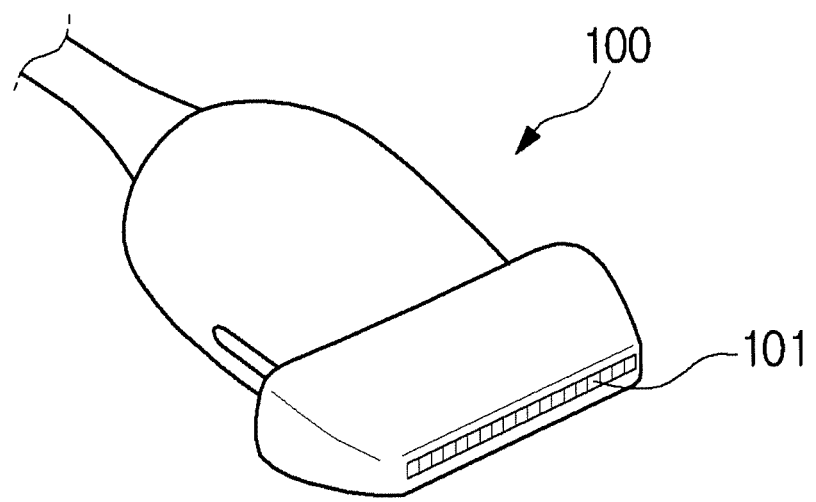
FIG. 2 shows the outer appearance of an ultrasound probe including a 1 Dimensional (1D) array transducer.
Figure 3:
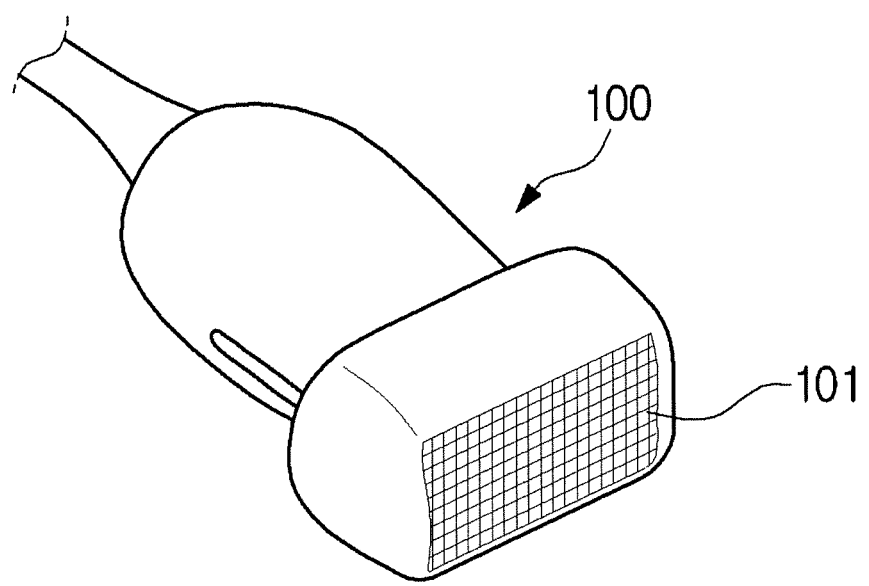
FIG. 3 shows the outer appearance of an ultrasound probe including a 2 Dimensional (2D) array transducer.

FIG. 2 shows the outer appearance of an ultrasound probe including a 1 Dimensional (1D) array transducer, and FIG. 3 shows the outer appearance of an ultrasound probe including a 2 Dimensional (2D) array transducer.

The ultrasound probe 100 may contact the surface of the object ob, and transmit and receive ultrasound signals.

More specifically, the ultrasound probe 100 may convert a pulse signal received from the main body 200 into an ultrasound signal, transmit the ultrasound signal to a specific part inside the object ob, receive an echo ultrasound signal reflected from the specific part inside the object ob, again convert the echo ultrasound signal into a pulse signal, and then transfer the pulse signal to the main body 200. However, this operation is only exemplary, and the ultrasound probe 100 may transmit/receive ultrasound signals and echo ultrasound signals to/from the main body 200.

Herein, the echo ultrasound signal may be an ultrasound signal which is a Radio Frequency (RF) signal reflected from the object ob, although not limited to this. That is, the echo ultrasound signal may include any reflected signal of an ultrasound signal transmitted to the object ob.

The ultrasound probe 100 may include a transducer array to convert an electrical pulse signal into an ultrasound signal and vice versa, in order to transmit an ultrasound signal to the inside of the object ob. The transducer array may be configured with a single transducer element or a plurality of transducer elements.

The ultrasound probe 100 may generate an ultrasound signal through the transducer array, transmit the ultrasound signal to the object ob using a target part inside the object ob as a focus point, and receive an echo ultrasound signal reflected from the target part inside the object ob through the transducer array.

If the echo ultrasound signal arrives at the transducer array, the transducer array may vibrate at a predetermined frequency corresponding to the frequency of the echo ultrasound signal, and output alternating current of a frequency corresponding to the vibration frequency. Accordingly, the transducer array may convert the echo ultrasound signal into an echo signal which is a predetermined electrical signal.

Meanwhile, the transducer array may be a 1D array or a 2D array. According to an embodiment, the transducer module 101 may include a 1D transducer array as shown in FIG. 2.

Each of transducer elements constituting the 1D transducer array can convert an ultrasound signal into an electrical signal and vice versa. For this, the transducer element may be a magnetostrictive ultrasonic transducer using the magnetostrictive effect of a magnetic material, a piezoelectric ultrasonic transducer or a piezoelectric Micromachined Ultrasonic Transducer (pMUT) using the piezoelectric effect of a piezoelectric material, or a capacitive Micromachined Ultrasonic Transducer (cMUT) that transmits and receives ultrasonic waves using vibration of several hundreds or thousands of micromachined thin films.

Meanwhile, the 1D array may be linearly aligned, as shown in FIG. 2, or may be convexly aligned. In all of both cases, the ultrasound probe 100 may operate according to the same operation principle, however, if the ultrasound probe 100 includes a convex transducer module 101, an ultrasound signal irradiated from the transducer module 101 may be in the shape of a fan, and accordingly, an ultrasound image may also be created in the shape of a fan.

As another example, the transducer module 101 may include a 2D transducer array, as shown in FIG. 3. If the transducer module 101 includes a 2D transducer array, the inside of the object ob may be three-dimensionally imaged. Also, although the transducer array of the ultrasound probe 100 is one-dimensionally aligned, the ultrasound probe 100 may move the 1D transducer array mechanically to acquire volume information about the inside of the object ob, and transfer an echo ultrasound signal capable of creating a 3D ultrasound image to the main body 200.

Each of transducer elements constituting the 2D transducer array may be the same as each of the transducer elements constituting the 1D transducer array, and accordingly, a detailed description thereof will be omitted.

Hereinafter, the internal configurations of the ultrasound probe 100 and the ultrasound imaging apparatus 10 including the ultrasound probe 100 will be described in more detail.

Figure 4:
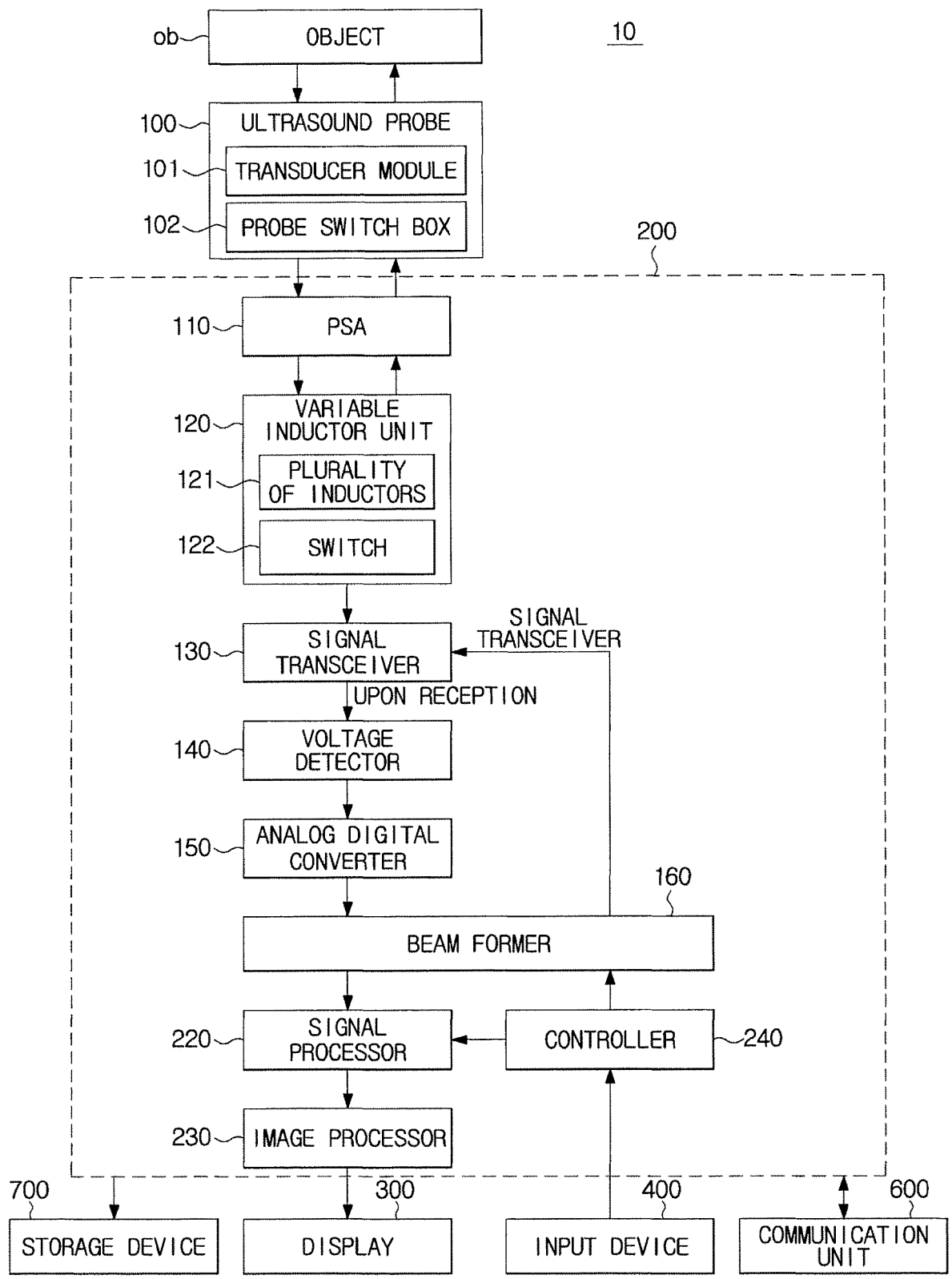
FIG. 4 is a block diagram of an ultrasound imaging apparatus according to an embodiment of the present disclosure.
Figure 5:
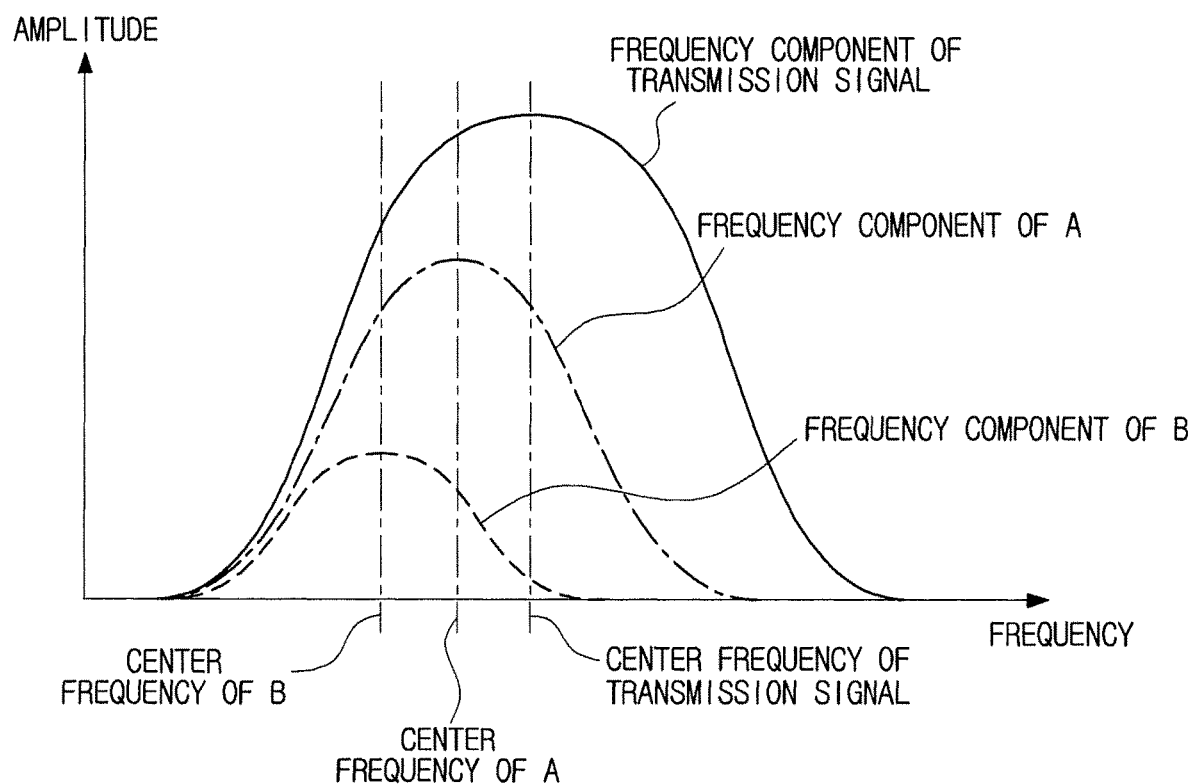
FIG. 5 is a view for describing a process in which the center frequency of a transmission/reception ultrasound signal moves according to the depth of an object ob, according to an embodiment of the present disclosure.
Figure 6:
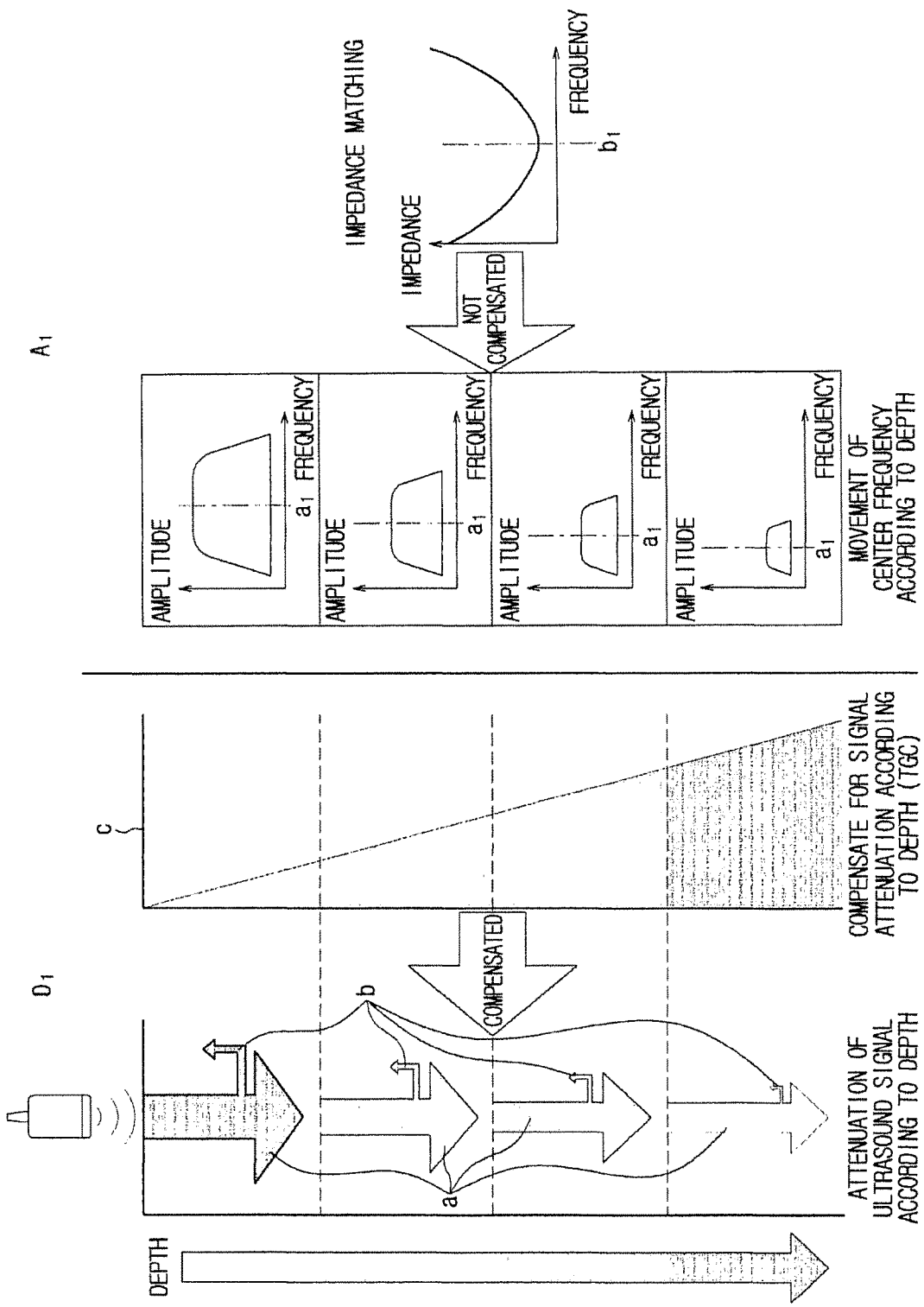
FIGS. 6 and 7 are views for describing a process of changing inductance for impedance matching with an ultrasound probe during a transmission/reception time period of an ultrasound signal, according to an embodiment of the present disclosure.
Figure 7:
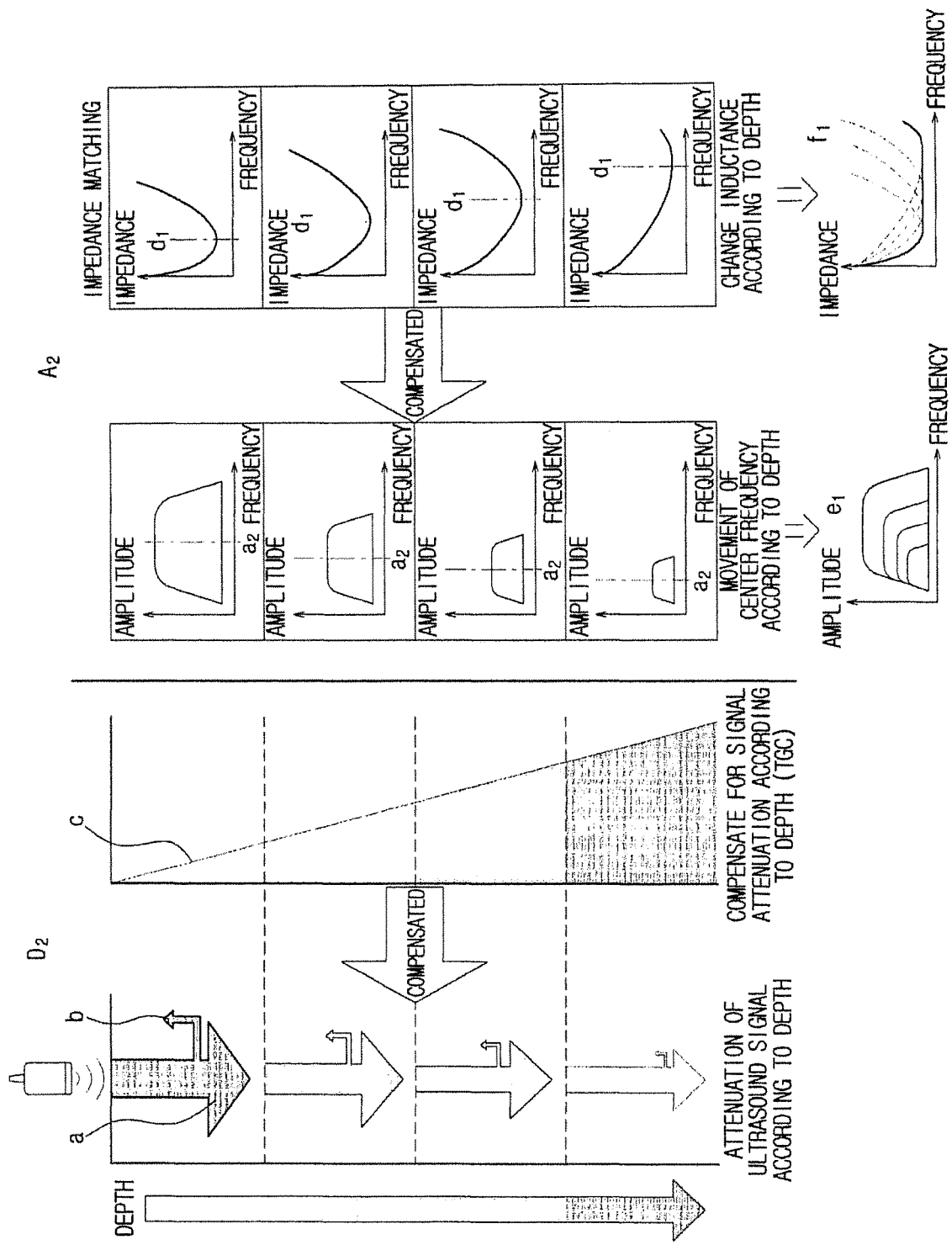

FIG. 4 is a block diagram of an ultrasound imaging apparatus according to an embodiment of the present disclosure, FIG. 5 is a view for describing a process in which the center frequency of a transmission/reception ultrasound signal moves according to the depth of an object ob, according to an embodiment of the present disclosure, FIGS. 6 and 7 are views for describing a process of changing inductance for impedance matching with an ultrasound probe during a transmission/reception time period of an ultrasound signal, according to an embodiment of the present disclosure.

Hereinafter, the ultrasound imaging apparatus 10 for transmitting/receiving an ultrasound signal to/from the ultrasound probe 100, and successively changing inductance using a plurality of inductors for impedance matching with the ultrasound probe 100 during a transmission/reception time period of the ultrasound signal will be described in detail with reference to FIGS. 4 to 7.

Referring to FIG. 4, the ultrasound imaging apparatus 10 may include the ultrasound probe 100 configured to transmit ultrasonic waves to an object ob and receive an echo ultrasound signal reflected from the object ob to acquire information about the object ob, and the main body 200 including a plurality of components, and configured to change the inductance of a variable inductor device 120 for impedance matching between the ultrasound probe 100 and the main body 200.

The ultrasound probe 100 may include the transducer module 101 included in the housing h, and the probe switch box 102 to which the ultrasound probe 100 is connected.

Also, the ultrasound probe 100 may receive an ultrasound signal from a signal transceiver 130 through a Probe Selection Assembly (PSA) 110 and a variable inductor device 120, as shown in FIG. 4. Also, the ultrasound probe 100 may transmit an ultrasound signal to the signal transceiver 130 through the PSA 110 and the variable inductor device 120.

However, this operation is only exemplary, and the ultrasound probe 100 may transmit/receive an ultrasound signal directly to/from the signal transceiver 130, according to another configuration.

Also, the ultrasound probe 100 may convert a received pulse signal into an ultrasound signal, and transmit the ultrasound signal to the object ob, or may receive an echo ultrasound signal reflected from the object ob and convert the echo ultrasound signal into a pulse signal.

The transducer module 101 has been described above, and accordingly, a detailed description thereof will be omitted.

The probe switch box 102 may be disposed at the end of the cable 170 connecting the ultrasound probe 100 to the main body 200, and accordingly, the ultrasound probe 100 may be connected to the probe switch box 102.

The main body 200, which is an apparatus to control the ultrasound probe 100 or to accommodate components required for creating an ultrasound image based on a signal received from the ultrasound probe 100, may be connected to the ultrasound probe 100 through the cable 170.

Also, the ultrasound probe 100 may include one or more processors. Accordingly, the ultrasound probe 100 may include one or more processors that perform the same functions as a controller installed in the main body 200, so that the ultrasound probe 100 can be controlled independently from the controller 240 of the ultrasound imaging apparatus 10.

Hereinafter, the PSA 110, the variable inductor device 120, the signal transceiver 130, a voltage detector 140, an analog-digital converter 150, a beam former 160, a signal processor 220, an image processor 230, and the controller 240, which are included in the main body 200, will be described, and also, the display 300, the input device 400, a communication unit 600, and a storage device 700 will be described. The main body 200 may further include the display 300, the input device 400, the communication unit 600, and the storage device 700, however, the display 300, the input device 400, the communication unit 600, and the storage device 700 may be separated from the main body 200. Hereinafter, repeated descriptions will be omitted.

If there are a plurality of ultrasound probes 100, the PSA 110 may selectively operate one of the plurality of ultrasound probes 100. Accordingly, the PSA 110 may include a relay switch for selecting one of the plurality of ultrasound probes 100. Also, the PSA 110 may receive a control command from the controller 240, and transmit an operation command to an ultrasound probe 100 selected from among the plurality of ultrasound probes 100.

The variable inductor device 120 may include a plurality of inductors 121, and at least one switch 122 to selectively connect the plurality of inductors 121 to one another. Also, the variable inductor device 120 may selectively connect at least one of the plurality of inductors 121 according to operation of the at least one switch 122 to thus change inductance. Also, the variable inductor device 120 may change inductance using the plurality of inductors 121 and the switch 122 to selectively connect the plurality of inductors 121.

The plurality of inductors 121 may have a multi-layer structure formed by stacking inductors. Also, the plurality of inductors 121 may have different inductance values. Also, the plurality of inductors 121 may be connected in series or in parallel. The plurality of inductors 121 may be selectively connected to one another by the switch 122 to thereby changing total inductance.

For example, the plurality of inductors 121 may include 8 inductors having inductance values of 0.1 μH, 0.2 μH, 0.3

μH, 0.4 μH, 1 μH, 2 μH, 3 μH, and 4 μH, respectively, or 7 inductors having inductance values of 0.1 μH, 0.2 μH, 0.3 μH, 0.4 μH, 2 μH, 3 μH, and 4 μH, respectively. The inductance values may be combined to decide a variable range of inductance, and the variable range of inductance may be decided within a range from 0 μH to 11 μH.

However, this is only exemplary, and the number of the plurality of inductors 121 may change according to the design so that the variable range of inductance may also change accordingly.

The at least one switch 122 may be disposed between the plurality of inductors 121. Also, the at least one switch 122 may include at least one of a Micro Electromechanical Systems (MEMS) switch and a Field Effect (FET) switch. Also, the at least one switch 122 may receive an on/off operation signal from the controller 240 to selectively connect at least one of the plurality of inductors 121.

Also, the variable inductor device 120 may successively change inductance for impedance matching between the ultrasound probe 100 and the main body 200 during a transmission/reception time period of an ultrasound signal.

More specifically, the variable inductor device 120 may successively change inductance, while the ultrasound probe 100 converts a pulse signal received from the signal transceiver 130 into an ultrasound signal, receives an echo ultrasound signal reflected from an object ob, converts the echo ultrasound signal into a pulse signal, and then transmits the pulse signal to the signal transceiver 130. The reason why the variable inductor device 120 successively changes inductance is to match impedance between the ultrasound probe 100 and the main body 200.

The impedance matching is to optimize impedance of the ultrasound probe 100 and the main body 200, in order to maintain the waveform of a transmission/reception ultrasound signal within an operating frequency range of the ultrasound imaging apparatus 10 and to improve the sensitivity of the transmission/reception ultrasound signal.

The reason of optimizing impedance is because the ultrasound probe 100 seen from the ultrasound imaging apparatus 10 can be considered as a single capacitor by a capacitor component of the transducer module 101 and a capacitor component of the cable 170 connecting the ultrasound probe 100 to the main body 200. If impedance mismatches, a transmission ultrasound signal may be subject to energy loss and waveform distortion. Accordingly, the ultrasound imaging apparatus 10 can acquire an optimal ultrasound image through impedance matching.

The impedance matching between the ultrasound probe 100 and the main body 200 may be conducted by installing the variable inductor device 120 in the ultrasound imaging apparatus 10 and combining the plurality of inductors 121 to change inductance, thereby canceling a capacitive reactance component.

Also, according to a typical technique, an inductor used for impedance matching between the ultrasound probe 100 and the main body 200 in order to maintain the waveforms of transmission/reception ultrasonic waves within an ultrasonic frequency range for operating the ultrasound probe 100 and to improve the transmission/reception sensitivity is included in the ultrasound probe 100. Also, in the typical technique, the inductor has a fixed inductance value.

In other words, when the signal transmitter 130 transmits/receives an ultrasound signal to/from the ultrasound probe 100, inductance is fixed during a transmission/reception time period of the ultrasound signal.

However, the ultrasound imaging apparatus 10 according to an embodiment of the present disclosure can successively change inductance through the variable inductor device 120, for impedance matching between the ultrasound probe 100 and the main body 200, during a transmission/reception time period of an ultrasound signal for creating an ultrasound image.

Also, the variable inductor device 120 may successively change inductance according to a change in center frequency of an ultrasound signal received from the ultrasound probe 100.

The change in center frequency of the received ultrasound signal may be caused by attenuation of an echo ultrasound signal reflected from the object ob, and particularly, signal attenuation may be significant in the high frequency band of the received ultrasound signal. Accordingly, in order to compensate for the signal attenuation, the variable inductor device 120 may receive a control signal from the controller 240 to change total inductance.

More specifically, the ultrasound probe 100 may receive a pulse signal from the signal transceiver 130, and convert the pulse signal to generate an ultrasound signal. Also, the ultrasound probe 100 may transmit the ultrasound signal to the object ob. The ultrasound signal may move through the object ob, that is, medium to attenuate according to a depth to which the ultrasound signal penetrates the medium so that the sound pressure of the ultrasound signal is lowered, wherein a degree of attenuation of the ultrasound signal may be proportional to the penetration depth and a transmission frequency.

Also, the echo ultrasound signal means a reflection signal of the ultrasound signal irradiated to the object ob. Also, the degree of attenuation of the received echo ultrasound signal may increase sharply in correspondence to the attenuation of the ultrasound signal and the movement distance of the reflected ultrasound signal. Accordingly, the center frequency of the echo ultrasound signal may be greatly lowered.

Referring to a graph shown in FIG. 5, the frequency components of a ultrasound signal transmitted from the signal transceiver 130 may have a relatively highest center frequency, and range from a low frequency band to a high frequency band, compared to other echo ultrasound signals (the frequency components of a signal A and the frequency components of a signal B).

Meanwhile, in the case of the echo ultrasound signals (the frequency components of the signal A and the frequency components of the signal B), which are signals reflected from the object ob and then received by the signal transceiver 130, the center frequencies of the echo ultrasound signals may be lowered from a high frequency band to a low frequency band, and the amplitudes of the echo ultrasound signals may also be reduced, according to distances to locations at which the echo ultrasound signals are reflected from the object ob, that is, as the echo ultrasound signals are received from a longer distance rather than a shorter distance.

The phenomenon in which the center frequency of a received ultrasound signal is lowered from a high frequency band to a low frequency band in proportion to a movement distance to an object ob can be compensated by changing inductance when the ultrasound signal is received. This operation will be described in detail with reference to FIGS. 6 and 7, later.

Also, at least one of the frequency and waveform of an ultrasound signal may be changed according to an application based on a diagnosis part (for example, the heart, blood vessels, abdomen, thyroid, fetus, etc.). For example, in order to observe the shape of an object ob, spatial resolution may be required, and a short pulse waveform may be transmitted to diagnose the heart, the blood vessels, etc. Due to the short pulse, axial resolution may increase, and a wider signal bandwidth may enable reception of signals from a deeper part. In the case of a harmonic image, the short pulse waveform will be more effective since different transmission and reception frequencies are used. Meanwhile, in order to observe organs in the abdomen that do not move, contrast resolution may be required since the texture of tissues is more important than the shapes of the organs, and accordingly, a Gaussian pulse waveform that is gently curved may be used.

As such, although different frequencies and waveforms of ultrasound signals are required according to the purposes of diagnosis, a fixed inductor having inductance selected for a predetermined frequency or a specific frequency band may have limitation in transmitting/receiving signals for acquiring an optimal image.

Accordingly, the ultrasound imaging apparatus 10 may change inductance according to a use frequency using the variable inductor device 120 in order to acquire an optimal ultrasound image, in consideration of the frequency and waveform of an ultrasound signal required according to the purpose of diagnosis.

As described above, the variable inductor device 120 may successively change inductance for impedance matching between the ultrasound probe 100 and the main body 200 during a transmission/reception time period of an ultrasound signal, and the variable inductor device 120 may also successively change inductance according to a change in center frequency of an ultrasound signal received from the ultrasound probe 100.

The operation will be described with reference to FIGS. 6 and 7, below. FIG. 6 is a view for describing a typical technique in which a fixed inductor is applied to an ultrasound imaging apparatus.

The left part D1 of FIG. 6 is a view for describing a process of compensating for attenuation in amplitude of a signal generated according to a depth to which an ultrasound signal penetrates an object ob.

A transmission ultrasound signal attenuates according to a depth to which the transmission ultrasound signal penetrates an object ob (a). Also, as described above, the attenuated transmission ultrasound signal is reflected from the object ob and then received, wherein a degree of attenuation of an echo ultrasound signal reflected from the object ob may be greater than a degree of attenuation of the transmission ultrasound signal, according to a movement distance of the echo ultrasound signal (b).

If the amplitude of the echo ultrasound signal attenuates, the voltage detector 140 may amplify the echo ultrasound signal by a degree of attenuation in proportion to depth from an analog terminal (DGC), or in proportion to time (TGC), in order to compensate for the attenuation in amplitude of the echo ultrasound signal (c).

However, movement of the center frequency generated by the attenuation of the echo ultrasound signal, in other words, movement a1 of the center frequency of the echo ultrasound signal from a high frequency band to a low frequency band may be not compensated (A1). The reason is because impedance between the ultrasound probe 100 and the main body 200 matches at a single center frequency b1 due to the fixed inductor in the ultrasound imaging apparatus 10.

FIG. 7 is a view for describing a case in which the variable inductor device 120 is applied to the ultrasound imaging apparatus 10 according to an embodiment of the present disclosure.

The left part D2 of FIG. 7 is a view for describing a process of compensating for attenuation in amplitude of a signal generated according to a depth to which an ultrasound signal penetrates an object ob. A phenomenon shown in the left part D2 of FIG. 7 is the same as that shown in the left part D1 of FIG. 6, and accordingly, a detailed description thereof will be omitted.

However, unlike the typical technique, movement of a center frequency generated by attenuation of an echo ultrasound signal according to a penetration depth of an ultrasound signal, in other words, movement a2 of the center frequency of an echo ultrasound signal from a high frequency band to a low frequency band can be compensated (A2). Such a compensation is achieved as the variable inductor device 120 of the ultrasound imaging apparatus 10 varies the inductance so that an impedance matching is performed according to a frequency band with a moved centered frequency.

Accordingly, the ultrasound imaging apparatus 10 according to an embodiment of the present disclosure can perform impedance matching between the ultrasound probe 100 and the main body 200 at any frequency band (f1), so that a constant signal amplitude and a constant center frequency can be maintained regardless of a depth to which an ultrasound signal penetrates an object ob (e1).

Also, the variable inductor device 120 may be included in any component in the main body 200 of the ultrasound imaging apparatus 10. For example, the variable inductor device 120 may be included in the PSA 110. Also, the variable inductor device 120 may be included in the ultrasound probe 100, for example, in the probe switch box 102. However, the reason of installing the variable inductor device 120 in the main body 200 is because the variable inductor device 120 can be applied to any ultrasound probe 100 connected to the main body 200 in order to acquire an optimal ultrasound image. However, if the variable inductor device 120 is installed in the probe switch box 12, the variable inductor device 120 can be applied to only the probe switch box 102, which is inefficient.

In an irradiation mode, the signal transceiver 130 may transmit an ultrasound signal received from the beam former 160 to the variable inductor device 120, according to a control signal from the controller 240 of the main body 200. However, the signal transceiver 130 may transmit an ultrasound signal received from the beam former 160 to the ultrasound probe 100, according to another configuration.

Also, in a reception mode, the signal transceiver 130 may transmit an ultrasound signal received from the variable inductor device 120 to the voltage detector 140, according to a control signal from the controller 240 of the main body 200.

However, the operation is only an embodiment, and the signal transceiver 130 may transmit/receive ultrasound signals to/from the ultrasound probe 100, not via the PSA 110 and the variable inductor device 120, according to another configuration.

The voltage detector 140 may sense current output from the transducer module 101. The voltage detector 140 may be implemented as an amplifier to amplify a voltage according to output current.

Also, the voltage detector 140 may further include a pre-amplifier to amplify an analog signal of a small amplitude, and the pre-amplifier may be a Low Noise Amplifier (LNA).

Also, the voltage detector 140 may further include a Variable Gain Amplifier (VGA) (not shown) to control a gain value according to an input signal. The VGA may use Time Gain Compensation (TGC) to compensate for gain according to a focus point or a distance to a focus point, although not limited to this.

The analog-digital converter 150 may convert an analog voltage output from the voltage detector 140 into a digital signal. Also, the analog-digital converter 150 may transfer the digital signal in the form of an electrical signal to the beam former 160.

In FIG. 4, a digital signal converted by the analog-digital converter 150 is input to the beam former 160, however, an analog signal delayed by the beam former 160 may be input to the analog-digital converter 140.

Also, in FIG. 4, the analog-digital converter 150 is included in the main body 200, however, the analog-digital converter 150 may be included in the ultrasound probe 100. In this case, the analog-digital converter 150 may convert an analog signal focused by an adder to a digital signal.

The beam former 160 may transmit the digital signal converted by the analog-digital converter 150, in the form of an electrical signal, to the signal processor 220. Also, the beam former 160 may receive a control command for transmitting an ultrasound signal to the signal transceiver 130, from the controller 240, and accordingly, the beam former 160 may transmit an ultrasound signal to the signal transceiver 130.

Also, the beam former 160 may apply appropriate delay time to an ultrasound signal to be irradiated or a received echo ultrasound signal, in order to cause ultrasonic waves generated in the transducer module 101 to be focused on a target part of an object ob at desired time, or to compensate for a difference between times at which echo ultrasound signals reflected from the target part of the object ob arrive at the transducer module 101.

In the ultrasound imaging apparatus 10 shown in FIG. 4, the beam former 160 may be included in the ultrasound probe 100 corresponding to a front-end, as described above, or in the main body 200 corresponding to a back-end. However, the entire or a part of the components of the beam former 160 may be included in any one of the front-end and the back-end.

The signal processor 220 may convert the focused digital signal received from the analog-digital converter 150 to a format suitable for image processing. For example, the signal processor 220 may perform filtering for removing noise signals except for a desired frequency band.

Also, the signal processor 220 may be implemented as a Digital Signal Processor (DSP), and perform envelope detection processing for detecting the magnitude of echo ultrasonic waves based on the focused digital signal to create ultrasound image data.

The image processor 230 may create an ultrasound image based on the ultrasound image data created by the signal processor 220 so that a user (for example, a doctor or a patient) can visually examine the inside of the object ob, for example, a human body.

The image processor 230 may transfer the ultrasound image created based on the ultrasound image data to the display 300.

Also, the image processor 230 may further perform additional image processing on the ultrasound image, according to another embodiment of the present disclosure. For example, the image processor 230 may further perform post-processing for correcting or re-adjusting the contrast, brightness, or sharpness of the ultrasound image.

The additional image processing by the image processor 230 may be performed according to a predetermined setting or according to a user's instruction or command input through the input device 400.

The controller 240 may control overall operations of at least one of the ultrasound imaging apparatus 10 and the ultrasound probe 100. For example, the controller 240 may control operations of the beam former 160, the signal processor 220, the image processor 230, the ultrasound probe 100, and the display 300. Also, the controller 240 may control operation of the switch 122 of the variable inductor device 120. The controller 240 may control operation of the switch 122 of the variable inductor device 120 to enable the variable inductor device 120 to change inductance. More specifically, the controller 240 may control the variable inductor device 120 to successively change inductance for impedance matching between the ultrasound probe 100 and the main body 200 during a transmission/reception time period of an ultrasound signal.

According to an embodiment, the controller 240 may control operation of the ultrasound imaging apparatus 10 according to a predetermined setting, or may generate a predetermined control command according to a user's instruction or command input through the input unit 400 and then control operation of the ultrasound imaging apparatus 10. Also, the controller 240 may control operation of the ultrasound probe 100, in addition to operation of the ultrasound imaging apparatus 10.

Also, if the ultrasound imaging apparatus 10 is paired with an external device by a communication method, such as wireless communication, Bluetooth, NFC, infrared communication, and the like, the controller 240 may control at least one of the ultrasound imaging apparatus 10 and the ultrasound probe 100 through the external device. Also, the controller 240 may control the communication unit 600 to transmit various information about the ultrasound imaging apparatus 10 to the external device.

The controller 240 may include a processor, Read Only Memory (ROM) to store control programs for controlling the ultrasound imaging apparatus 10, and Random Access Memory (RAM) to store signals or ultrasound image data input from the ultrasound probe 100 or the input device 400 of the ultrasound imaging apparatus 10, or used as a storage area for various tasks that are performed by the ultrasound imaging apparatus 10. In the above description, the controller 240 is included in the main body 200, however, the controller 240 may be included in the ultrasound probe 100. Also, the controller 240 may be a single processor, or may be configured with a plurality of processors.

Also, the controller 240 may include a graphic processing board including a processor, ROM, or RAM mounted on a separate circuit board electrically connected to the controller 240.

The processor, ROM, and RAM may be connected to each other through internal buses.

Also, the controller 240 may be used as a term indicating a component including a processor, ROM, and RAM.

Also, the controller 240 may be used as a term indicating a component including a processor, ROM, RAM, and a processing board.

The display 300 may display various information received from the controller 240. Also, the display 300 may display at least one of the ultrasound image acquired from the ultrasound probe 100 and information about the ultrasound image.

The display 300 may display the ultrasound image created by the image processor 230 so that the user can visually examine the inside structure or tissue of the object ob. Also, the display 300 may display various data and images related to the ultrasound imaging apparatus 10.

More specifically, the display 300 may display data such as the elasticity of a Region of Interest (ROI) of the object ob, in addition to the inside structure or tissue of the object ob, so that the user can check information about the object ob as a numerical value, while visually examining the object ob.

The display 300 may be implemented as a Cathode Ray Tube (CRT), a Liquid Crystal Display (LCD), a Light Emitting Diode (LED) display, a Plasma Display Panel (PDP) display, an Organic Light Emitting Diode (OLED) display, etc., which are well-known in the art.

If the display 300 is a touch screen type, the display 300 may perform the functions of the input device 400. That is, the main body 200 may receive various commands from the user through at least one of the display 300 and the input device 400.

Also, if the display 300 is used as the input device 400, the display 300 may display at least one of a User Interface (UI) screen and a selection screen for receiving the user's inputs. In this case, the user may touch at least one of an icon, an image, and text displayed on the display 300 to enable at least one of the ultrasound imaging apparatus 10 and the ultrasound probe 100 to perform a predetermined function.

Also, the main body 200 may include a voice recognition sensor (not shown) to receive a voice command from the user.

The display 300 may display an ultrasound image about a target part of the object ob. The ultrasound image displayed on the display 300 may be a 2D ultrasound image or a 3D ultrasound image. The display 300 may display various ultrasound images according to operation modes of the ultrasound imaging apparatus 10. Also, the display 300 may display information related to an operation state of the ultrasound probe 100, as well as a menu or guidance needed for ultrasonic diagnosis.

According to an embodiment, the ultrasound image may include an Amplitude-mode (A-mode) image, a Brightness-mode (B-mode) image, a Motion-mode (M-mode) image, a Color-mode (C-mode) image, and a Doppler-mode (D-mode) image.

The A-mode image means an ultrasound image representing the amplitude of an ultrasound signal corresponding to an echo ultrasound signal, the B-mode image means an ultrasound image representing the amplitude of an ultrasound signal corresponding to an echo ultrasound signal as brightness, and the M-mode image means an ultrasound image representing the motion of an object ob according to time at a specific location. The D-mode image means an ultrasound image representing a moving object ob in the form of a waveform using the Doppler effect, and the C-mode image means an ultrasound image representing a moving object ob in the form of a color spectrum.

The input device 400 may receive various control commands, as well as setting information about the ultrasound probe 100, from the user.

Also, the input device 400 may receive at least one of commands for performing various operations of the ultrasound imaging apparatus 10 and commands for changing the setting information about the ultrasound probe 100.

The information may be transferred to the ultrasound probe 100 through a wired/wireless communication network, and the ultrasound probe 100 may be set based on the received information. Also, the main body 200 may receive various control commands such as a command for transmitting an ultrasound signal from the user, through the input device 400, and transfer the control commands to the ultrasound probe 100.

Meanwhile, the input device 400 may be implemented as a mouse, a keyboard, a foot switch, or a foot pedal. For example, the keyboard may be hardwarily implemented. The keyboard may include at least one of a switch, a key, a joystick, and a trackball. According to another example, the keyboard may be softwarily implemented, like a Graphic User Interface (GUI). In this case, the keyboard may be displayed on the display 300. The foot switch or the foot pedal may be disposed below the main body 200, so that the user can control the operation of the ultrasound imaging apparatus 10 using the foot pedal.

The input device 400 may receive a predetermined instruction or command from the user in order to control the ultrasound imaging apparatus 10. The input device 400 may include a user interface, such as a keyboard, a mouse, a trackball, a touch screen, and an input button or pedal of the ultrasound probe 100.

The communication unit 600 may include one or more components to enable communication with an external device. For example, the communication unit 600 may include at least one of a short-range communication module, a wired communication module, and a wireless communication module.

The short-range communication module may include various short-range communication modules to transmit/receive signals using a wireless communication network within a short distance range, such as a Bluetooth module, an Infrared communication module, a Radio Frequency Identification (RFID) communication module, a WLAN communication module, a NFC communication module, and a Zigbee communication module.

The wired communication module may include various cable communication modules, such as Universal Serial Bus (USB), High Definition Multimedia Interface (HDMI), Digital Visual Interface (DVI), Recommended Standard 232 (RS-232), Power Line Communication (PLC), and Plain Old Telephone Service (POTS), as well as various wired communication modules, such as a Local Area Network (LAN) module, a Wide Area Network (WAN) module, and a Value Added Network (VAN) module.

The wireless communication module may include wireless communication modules supporting various wireless communication methods, such as Global System for Mobile Communication (GSM), Code Division Multiple Access (CDMA), Wideband Code Division Multiple Access (WCDMA), Universal Mobile Telecommunications System (UMTS), Time Division Multiple Access (TDMA), and Long Term Evolution (LTE), as well as a Wi-Fi module and a Wireless broadband (Wibro) module.

The communication unit 600 may communicate with at least one of an external device and the ultrasound probe 100. Also, the communication unit 600 may transmit/receive data related to diagnosis of the object ob, such as an ultrasound image of the object ob acquired through the ultrasound probe 100, an echo ultrasound signal, Doppler data, and shear wave data. Also, the communication unit 600 may receive various information from the external device. The external device may include a wearable terminal, a wireless communication terminal, and a smart phone.

The storage device 700 may be implemented through at least one type of storage medium among a flash memory type, a hard disk type, a multimedia card micro type, card type memory (for example, Secure Digital (SD) or eXtreme Digital (XD) memory), RAM, Static Random Access Memory (SRAM), ROM, Electrically Erasable Programmable Read-Only Memory (EEPROM), Programmable Read-Only Memory (PROM), magnetic memory, a magnetic disk, and an optical disk. However, the storage device 700 is not limited to the above-mentioned devices, and may be implemented as any other type of storage device well-known in the art.

The storage device 700 may be memory implemented as a separate chip from the processor described above in regard of the controller 240, or may be implemented as the same chip as the processor. Also, the storage device 700 may store at least one of an ultrasound image of the object ob acquired by the ultrasound probe 100 and diagnosis data related to the ultrasound image. Also, the storage device 700 may store various settings related to the ultrasound imaging apparatus 10.

The ultrasound imaging apparatus 10 that successively changes inductance for impedance matching between the ultrasound probe 100 and the main body 200 during a transmission/reception time period of an ultrasound signal has been described above with reference to FIGS. 4 to 7.

Figure 8:
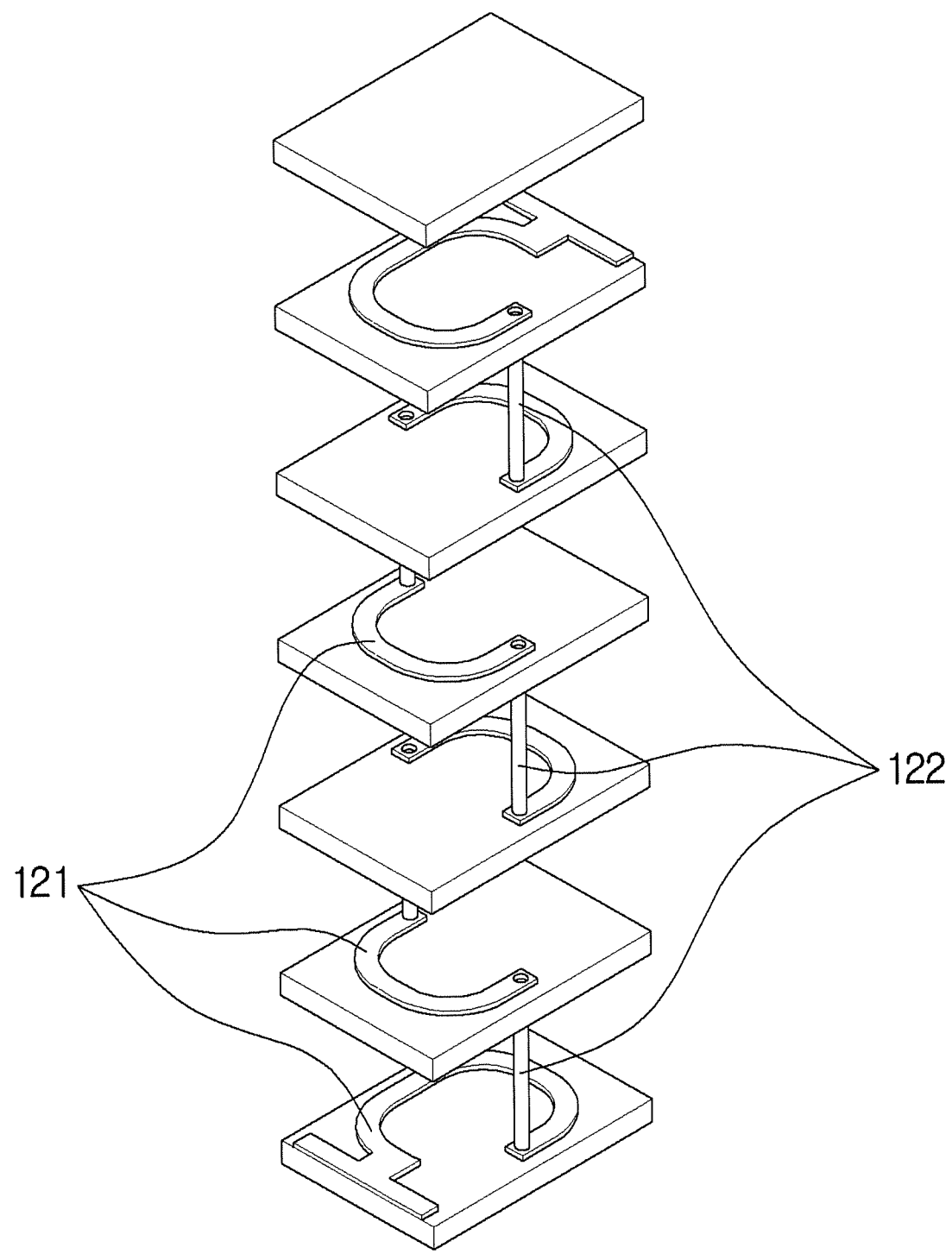
FIG. 8 shows a variable inductor device formed by stacking a plurality of inductors, according to an embodiment of the present disclosure.

FIG. 8 shows a variable inductor device formed by stacking a plurality of inductors, according to an embodiment of the present disclosure.

As described above, the variable inductor device 120 may include the plurality of inductors 121 and the at least one switch 122 connecting the plurality of inductors 121 to one another.

Referring to FIG. 8, the variable inductor device 120 may have a multi-layer structure formed by stacking the plurality of inductors 121. The multi-layer structure is aimed to minimize the volume of the variable inductor device 120 in the ultrasound imaging apparatus 10. Accordingly, a manufacturing cost of the ultrasound imaging apparatus can be reduced.

Also, the variable inductor device 120 may include the at least one switch 122 disposed between the plurality of inductors 121.

Also, the variable inductor device 120 may control the switch 122 disposed between the plurality of inductors 121 stacked on top of one another to selectively connect the plurality of inductors 121, thereby changing total inductance through a combination of the connected inductors 121. This operation will be described in detail with reference to FIG. 11, later.

Figure 9B:
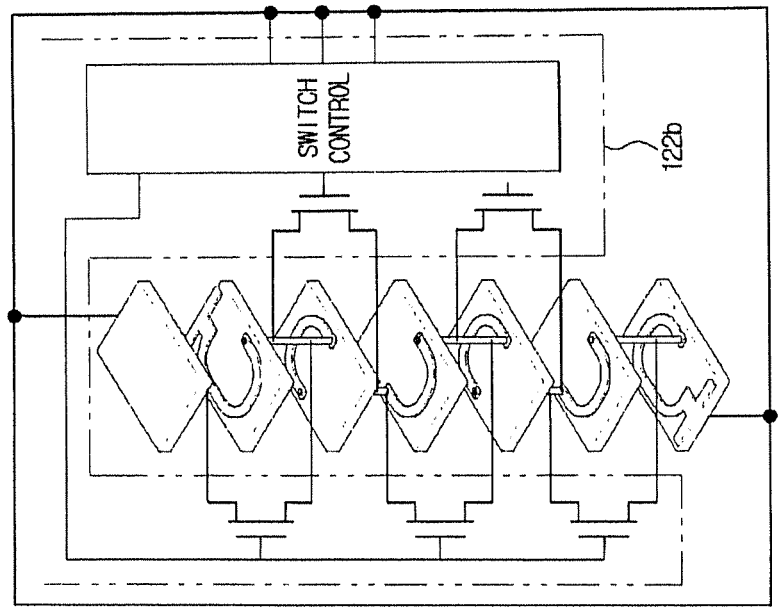
FIGS. 9A and 9B are views for describing various embodiments of at least one switch to selectively connect at least one of a plurality of inductors according to an embodiment of the present disclosure.
Figure 9A:
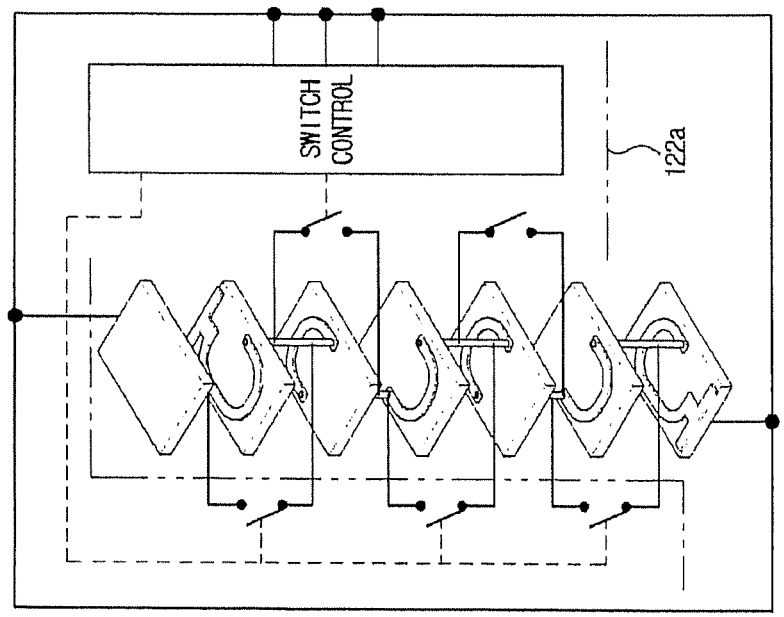

FIGS. 9A and 9B are views for describing various embodiments of at least one switch to selectively connect at least one of a plurality of inductors according to an embodiment of the present disclosure.

The switch 122 may be disposed between the plurality of inductors 122 stacked on top of one another. Also, the switch 122 may be turned on/off by receiving an operation control command from the controller 240 to thereby selectively connect each of the plurality of inductors 121 to another inductor 121. There may be provided a plurality of switches 122 respectively disposed between the plurality of inductors 121. In the above description, the switch 122 receives an operation control command from the controller 240, however, if a switch controller (not shown) is included in the variable inductor 120, the switch 122 may receive an operation command from the switch controller.

Also, the switch 122 may include various kinds of switches to selectively connect the plurality of inductors 121. More specifically, the switch 122 may include at least one of a MEMS switch 122a and a FET switch 122b, as shown in FIGS. 9A and 9B.

The MEMS switch 122a is a mechanical switch manufactured by a process of a micro electromechanical system. The MEMS switch 122a may be disposed between the plurality of inductors 122, as shown in FIG. 9A. The MEMS switch 122a may be used to individually connect the plurality of inductors 121 to one another.

Also, the FET switch 122b is a switch using a semiconductor method. The FET switch 122b may be disposed between the plurality of inductors 121, as shown in FIG. 9B. The FET switch 122b may be used to individually connect the plurality of inductors 121 to one another.

Also, at least one of the MEMS switch 122a and the FET switch 122b may receive a control command for performing on/off operation from the controller 240 to individually connect the plurality of inductors 121 to one another. Accordingly, the variable inductor device 120 may change inductance by selectively connecting the plurality of inductors 121. This operation will be described in detail with reference to FIGS. 11A and 11B, later.

Figure 10B:
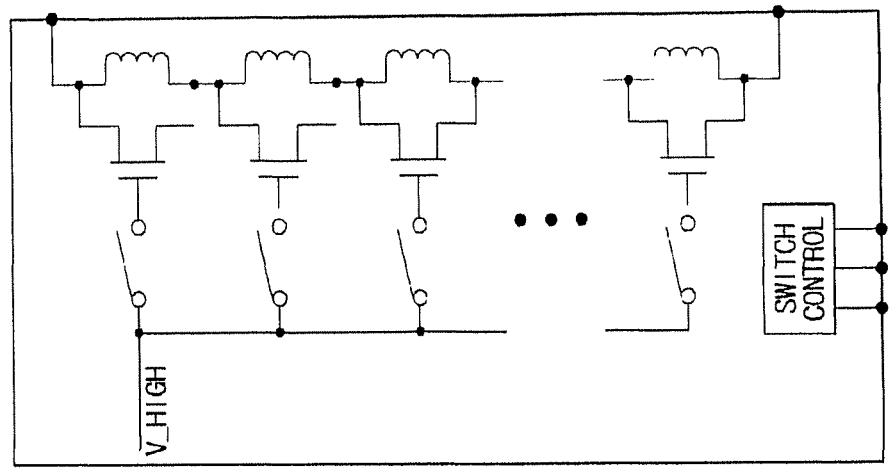
FIGS. 10A and 10B are views for describing various methods in which a variable inductor device according to an embodiment of the present disclosure changes inductance.
Figure 10A:
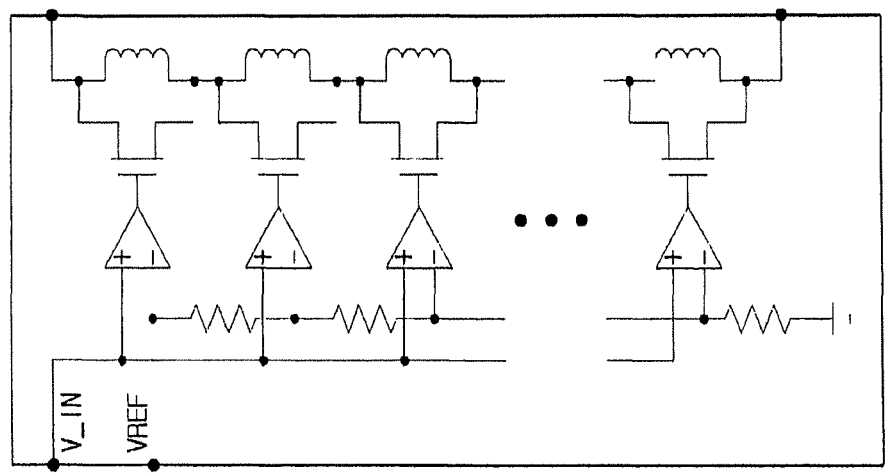

FIGS. 10A and 10B are views for describing various methods in which a variable inductor device according to an embodiment of the present disclosure changes inductance.

The variable inductor device 120 may include the plurality of inductors 121, and selectively connect at least one of the plurality of inductors 121 according to operation of the at least one switch 122 connecting the plurality of inductors 121 to change inductance. In other words, if the plurality of inductors 121 are connected in series, the variable inductor device 120 may control the switch 122 disposed between the plurality of inductors 121 to change total inductance.

Also, the variable inductor device 120 may combine the plurality of inductors 121 without using the switch 122 to change total inductance.

For example, as shown in FIG. 10A, the variable inductor device 120 may decide a comparison voltage of an OP-AMP used as a comparator, based on an input voltage V_IN and a reference voltage VREF, and open or close inductors connected in series according to the output result of the decided comparison voltage, thereby changing total inductance.

Also, as shown in FIG. 10B, the variable inductor device 120 may change total inductance using switches for directly controlling inductors connected in series.

Figure 11B:
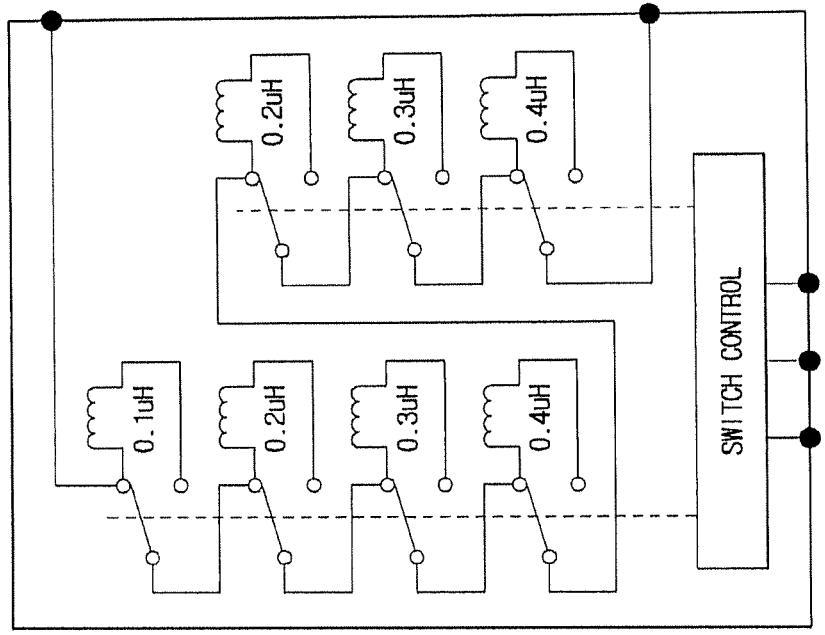
FIGS. 11A and 11B are views for describing a variable range of inductance of a variable inductor device according to an embodiment of the present disclosure.
Figure 11A:
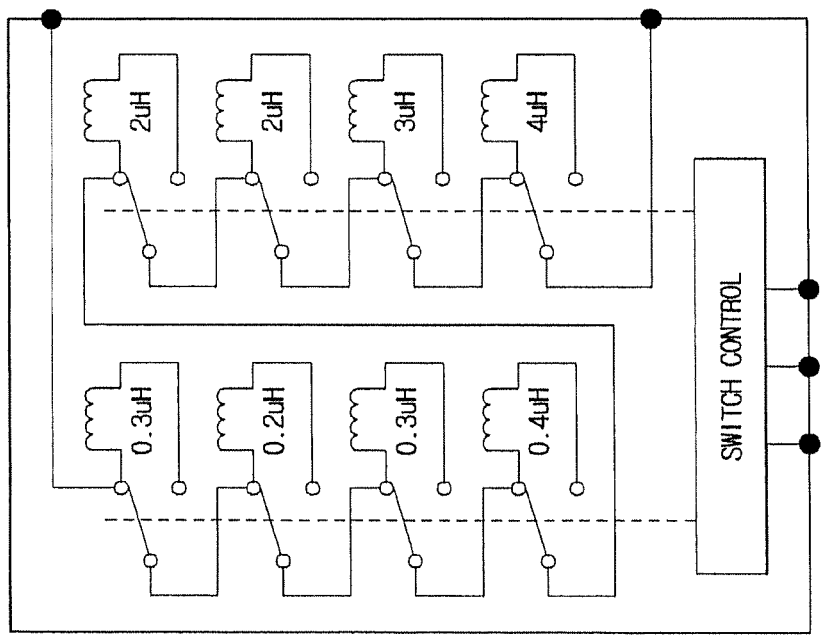

FIGS. 11A and 11B are views for describing a variable range of inductance of a variable inductor device according to an embodiment of the present disclosure.

The variable inductor device 120 may include the plurality of inductors 121, and selectively connect at least one of the plurality of inductors 121 according to operation of the at least one switch 122 connecting the plurality of inductors 121 to thereby change inductance. Also, the variable inductor device 120 may change inductance using various methods, without using the switch 122.

Referring to FIG. 11A, according to an embodiment of the variable inductor device 120, the variable inductor device 120 may include 8 inductors having impedance values of 0.1 µH, 0.2 µH, 0.3 µH, 0.4 µH, 1 µH, 2 µH, 3 µH, and 4 µH, respectively, and 8 switches connecting the 8 inductors. Also, the variable inductor device 120 may receive on/off operation commands for the 8 switches from the controller 240 to control the respective switches, thereby changing total inductance. A variable range of inductance may be decided within a range from 0 µH to 11 µH. Also, the variable range of inductance may change at intervals of 0.1 µH.

This is because when all of the 8 inductors are connected to one another by the switches, total inductance becomes maximum inductance of 11 µH, and when none of the 8 inductors is connected, total inductance becomes minimum inductance of 0 µH. Also, since a minimum interval of inductance is 0.1 µH, the inductance may change at intervals of 0.1 µH.

Referring to FIG. 11B, according to another embodiment of the variable inductor device 120, the variable inductor device 120 may include 7 inductors having inductance values of 0.1 µH, 0.2 µH, 0.3 µH, 0.4 µH, 2 µH, 3 µH, and 4 µH, respectively, and 7 switches. Also, the variable inductor device 120 may receive on/off operation commands for the 7 switches from the controller 240 to control the respective switches, thereby changing total inductance. A variable range of inductance may be decided within a range from 0 µH to 10 µH. Also, the variable range of inductance may change at intervals of 0.1 µH. This is because when all of the 7 inductors are connected to one another by the switches, total inductance becomes maximum inductance of 10 µH, and when none of the 7 inductors is connected, total inductance becomes minimum inductance of 0 µH. Also, since a minimum interval of inductance is 0.1 µH, the inductance may change at intervals of 0.1 µH. However, this is only an example of the plurality of inductors 121 of the variable inductor device 120, used to describe a method in which the variable inductor device 120 changes inductance. Accordingly, the variable inductor device 120 may be configured with more or less inductors 121, and have a wider variable range of inductance.

Figure 12:
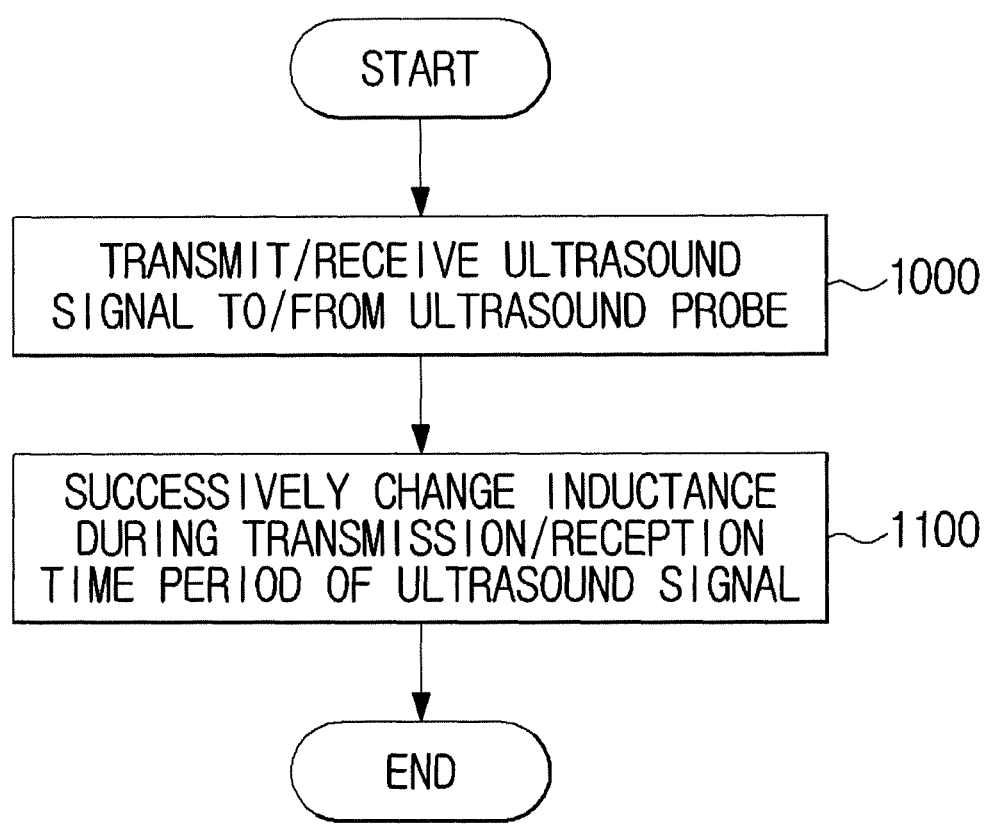
FIG. 12 is a flowchart illustrating a control method of an ultrasound imaging apparatus according to an embodiment of the present disclosure.

FIG. 12 is a flowchart illustrating a control method of an ultrasound imaging apparatus according to an embodiment of the present disclosure.

The ultrasound imaging apparatus 10 may transmit/receive an ultrasound signal to/from the ultrasound probe 100 through the signal transceiver 130, in order to acquire an optimal ultrasound image. The ultrasound probe 100 may convert a pulse signal into an ultrasound signal, and a received echo ultrasound signal into a pulse signal. Accordingly, the ultrasound imaging apparatus 10 may acquire an ultrasound image based on the transmitted/received ultrasound signal, in operation 1000.

Also, the ultrasound imaging apparatus 10 may change inductance of the variable inductor device 120 for impedance matching between the ultrasound probe 100 and the main body 200, while an ultrasound signal is transmitted and received through the signal transceiver 130 in order to acquire an ultrasound image, in operation 1100.

The ultrasound imaging apparatus 10 may change inductance of the variable inductor device 120 to compensate for attenuation of a received echo ultrasound signal. More specifically, the ultrasound imaging apparatus 10 may compensate for signal attenuation in a high frequency band, which is generated when the center frequency of a received ultrasound signal moves from the high frequency band to a low frequency band according to a depth which the ultrasound signal penetrates the object ob.

The ultrasound imaging apparatus to transmit/receive an ultrasound signal to/from the ultrasound probe and to successively change inductance using the plurality of inductors for impedance matching with the ultrasound probe during a transmission/reception time period of the ultrasound signal, and the control method of the ultrasound imaging apparatus have been described above.

According to the ultrasound imaging apparatus and the control method thereof as described above, by locating the variable inductor device in the ultrasound imaging apparatus to set an optimal inductance value according to a use frequency, an ultrasound image of optimal quality can be acquired.

Also, by changing a transmission ultrasound frequency and a waveform according to diagnostic purposes, it is possible to minimize the loss of a signal component in a reception band-of-interest.

Also, by correcting the movement of a center frequency according to a penetration depth of an ultrasound signal at an analog reception terminal, loss can be minimized compared to a typical technique.

Also, by reducing the number of inductors installed in the ultrasound imaging apparatus, it is possible to simplify the structure of the ultrasound imaging apparatus, while lowering a manufacturing cost of the ultrasound imaging apparatus.

The aforementioned descriptions are only for illustrative purposes, and it will be apparent that those skilled in the art can make various modifications thereto without changing the technical spirit and essential features of the present disclosure. Thus, it should be understood that the exemplary embodiments described above are merely for illustrative purposes and not for limitation purposes in all aspects. For example, each component described as a single type can be implemented in a distributed type, and components described as distributed can be implemented in a combined form.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. An ultrasound imaging apparatus comprising:
an ultrasound probe;
a signal transceiver configured to transmit/receive an ultrasound signal to/from the ultrasound probe; and
a variable inductor device configured to, while the ultrasound probe converts a pulse signal received from the signal transceiver into the ultrasound signal, receives an echo ultrasound signal reflected from an object, converts the echo ultrasound signal into the pulse signal, and then transmits the pulse signal to the signal transceiver, successively change inductance for impedance matching with the ultrasound probe during a transmission/reception time period of the ultrasound signal,
wherein the variable inductor device comprises:
a plurality of inductors which are stacked and have different inductance values; and
a plurality of switches, each of which is disposed between the plurality of inductors and connecting the plurality of inductors to one another,
wherein the variable inductor device selectively connects the plurality of inductors according to operation of the plurality of switches to change the inductance, and successively changes inductance according to a change in center frequency of the echo ultrasound signal received from the ultrasound probe.

2. The ultrasound imaging apparatus according to claim 1, wherein the plurality of switches comprise at least one of a MEMS switch and a FET switch.

3. The ultrasound imaging apparatus according to claim 1, wherein a variable range of the inductance is decided within a range from 0 µH to 11 µH.

4. The ultrasound imaging apparatus according to claim 1, wherein the plurality of inductors comprise 8 inductors having inductance values of 0.1 μH, 0.2 μH, 0.3 μH, 0.4 μH, 2 μH, 3 μH, and 4 μH, respectively, or 7 inductors having inductance values of 0.1 μH, 0.2 μH, 0.3 μH, 0.4 μH, 2 μH, 3 μH, and 4 μH, respectively.

5. The ultrasound imaging apparatus according to claim 1, further comprising a probe switch box to which the ultrasound probe is connected, wherein the variable inductor device is installed in the probe switch box.

6. A method of controlling an ultrasound imaging apparatus, comprising:

transmitting/receiving an ultrasound signal to/from an ultrasound probe; and successively changing inductance for impedance matching with the ultrasound probe during a transmission/reception time period of the ultrasound signal, while the ultrasound probe converts a pulse signal received from a signal transceiver into the ultrasound signal, receives an echo ultrasound signal reflected from an object, converts the echo ultrasound signal into the pulse signal, and then transmits the pulse signal to the signal transceiver, wherein the variable inductor device comprises:

a plurality of inductors which are stacked and have different inductance values; and a plurality of switches, each of which is disposed between the plurality of inductors and connecting the plurality of inductors to one another, wherein the changing of the inductance comprises selectively connecting the plurality of inductors according to operation of the plurality of switches to change the inductance, and successively changing inductance according to a change in center frequency of the echo ultrasound signal received from the ultrasound probe.

7. The method according to claim 6, wherein the plurality of switches comprise at least one of a MEMS switch and a FET switch.

8. The method according to claim 6, wherein a variable range of the inductance is decided within a range from 0 μH to 11 μH.

* * * * *